(12) United States Patent
Waldvogel et al.

(10) Patent No.: US 8,288,163 B2
(45) Date of Patent: Oct. 16, 2012

(54) APPARATUS AND METHOD FOR DETECTING TRIACETONE TRIPEROXIDE

(75) Inventors: Siegfried R. Waldvogel, Bonn (DE); Jürgen Lörgen, Mannheim (DE); Daniel Lubczyk, Bonn (DE); Klaus Müllen, Köln (DE); Roland Bauer, Eching (DE)

(73) Assignees: Rheinische Friedrich-Wilhelms-Universitaet Bonn, Bonn (DE); Max-Planck-Gesellschaft zur Foerderung der Wissenschaften E.V., Munich (DE)

( * ) Notice: Subject to any disclaimer, the term of this patent is extended or adjusted under 35 U.S.C. 154(b) by 131 days.

(21) Appl. No.: 12/865,412

(22) PCT Filed: Feb. 11, 2009

(86) PCT No.: PCT/EP2009/051594
§ 371 (c)(1), (2), (4) Date: Oct. 8, 2010

(87) PCT Pub. No.: WO2009/101118
PCT Pub. Date: Aug. 20, 2009

(65) Prior Publication Data
US 2011/0020944 A1    Jan. 27, 2011

(30) Foreign Application Priority Data
Feb. 11, 2008  (DE) .................. 10 2008 008 660

(51) Int. Cl.
*G01N 33/00* (2006.01)
(52) U.S. Cl. .......... 436/93; 436/130; 436/135; 436/181; 422/83; 422/88; 422/68.1; 73/24.01; 73/24.06
(58) Field of Classification Search .............. 436/93, 436/127, 130, 135, 149, 181; 422/68.1, 82.01, 422/83, 88, 98; 73/24.01, 24.06, 579
See application file for complete search history.

(56) References Cited

U.S. PATENT DOCUMENTS

| | | | |
|---|---|---|---|
| 6,316,268 B1 | 11/2001 | Yang et al. | |
| 6,526,828 B1 * | 3/2003 | Dayan et al. | 73/579 |
| 7,159,463 B2 | 1/2007 | Dayagi et al. | |
| 7,795,008 B2 * | 9/2010 | Dayagi et al. | 435/287.2 |
| 2006/0188399 A1 * | 8/2006 | Smid | 422/82.02 |
| 2006/0191320 A1 | 8/2006 | Pinnaduwage et al. | |
| 2011/0129937 A1 * | 6/2011 | Naaman et al. | 436/93 |

FOREIGN PATENT DOCUMENTS

| | | |
|---|---|---|
| DE | 101 09 534 A1 | 9/2002 |
| DE | 103 44 135 | 5/2005 |
| WO | 02 103340 A2 | 12/2002 |

* cited by examiner

*Primary Examiner* — Maureen Wallenhorst
(74) *Attorney, Agent, or Firm* — Norris McLaughlin & Marcus, P.A.

(57) ABSTRACT

The present invention relates to a device and process for the quick and reliable online detection of triacetone triperoxide (TATP).

12 Claims, 8 Drawing Sheets

Fig.12 ved piezoelectric effect, it is excited with a high
APPARATUS AND METHOD FOR DETECTING TRIACETONE TRIPEROXIDE This application is a 371 of PCT/EP2009/051594, filed Feb. 11, 2009, which claims foreign priority benefit under 35 U.S.C. §119 of the German Patent Application No. 10 2008 008 660.6 filed Feb. 11, 2008.

The present invention relates to a device and process for the quick and reliable online detection of triacetone triperoxide (TATP).

BACKGROUND OF THE INVENTION

Triacetone triperoxide (TATP) is an explosive that is very easily prepared and whose starting materials are readily available from drugstore articles (J. Zabicky, The chemistry of peroxides, John Wiley & Sons, Ltd; (2006); J. P. Agrawal, R. D. Hodgson, Organic Chemistry of Explosives, John Wiley & Sons, Ltd; (2007)). In addition, the starting materials (hydrogen peroxide, acetone and acid) are easily accessible in large amounts. Since this explosive is very sensitive to heat, impact and electrostatic discharge and requires no initial ignition and in addition has an explosive force comparable to that of TNT, it has no commercial or military relevance. However, due to its easy accessibility, it is often employed for terroristic purposes (e.g., Madrid, March 2004, London, July 2005). For this reason, a simple and quick online detection is necessary to avert dangers. Currently, the following detection methods are known (J. W. Gardner, J. Yinon (Eds.), Electronic Noses & Sensors for the Detection of Explosives, Kluwer Academic Publishers (2003); U.S. Pat. No. 7,159,463; Z. Lin et al., Anal. Chem. 65, 1546-1551 (1993); E. Uttenthaler et al., Biosensors & Bioelectronics 16, 735-743 (2001); DE-A-10109534):

Separation by RP-HPLC: Separation of a sample solution by RP-HPLC, decomposition of the TATP to hydrogen peroxide using a UV lamp, and determination of the hydrogen peroxide concentration by means of fluorescence spectroscopy. With this method, online measurement is not possible, since a sample solution needs to be prepared first, which can be examined further only with a great analytical effort.

Photometry: Treatment of a sample solution with peroxidase to destroy any traces of hydrogen peroxide, followed by irradiating this solution with a UV lamp to decompose TATP to hydrogen peroxide, and after the addition of a reagent solution, the sample is finally examined by photometry using a UV/Vis spectrometer. This method is portable, but the preparation of a sample solution is necessary. In addition, it requires a high analytical and apparative expenditure and is not suitable for online examinations.

E-3500: In this method, the sample is collected by manual swabbing (perhaps first danger of explosion)! After being applied to a metal disk, the analyte is thermally decomposed. With luminol, the oxidative decomposition products formed produce a chemoluminescence, which can be measured. Due to the necessary manual effort, online measurement is not possible, and application to personnel security screening is doubtful. This system does not have sufficient chemical selectivity, since there is no separation of the analytes. Thus, any substance that releases oxidizing decomposition products upon heating will be considered to be TATP.

Z nose: The z nose is a miniature variant of a gas chromatography with a down-stream SAW (surface acoustic wave) sensor as a mass-sensitive detector. The recognition of the substances is effected by comparing the retention times with an alkane standard. In this method too, the sample is preliminarily enriched before the actual analysis, so that online measurement is no longer possible.

Mini-nose: The mini-nose is a system constituted of two modules. The first of these modules is used to collect and enrich the sample. The second module analyzes the collected sample. In the second module, a sensor array consisting of several coated HFF oscillating quartz crystals is contained. For the measurement, the initially collected analyte is desorbed from module one into module two. After another 60 s of measuring time, the substance is then identified by means of main component analysis. In this case too, it is obvious that online examination is not possible due to the necessary enriching step.

WO02/103340 describes the use of an oscillating quartz crystal array with high frequency quartz crystals, so-called HFF quartz crystals. However, the sensor array used in each method is so insensitive that an enriching step is necessary before the actual detection.

However, every one of these methods involves drawbacks rendering it unfit for online monitoring: Either it requires a high analytical apparative expenditure, or it has a high detection limit (enriching may be necessary), or the measuring interval is too long, the method is non-selective before a chemically similar background, or it is required for TATP to be in a liquid phase. This means that detection of TATP traces in the air has been possible only after enriching or with a high analytical expenditure. This precludes the online monitoring of people and/or objects for averting dangers. Thus, a simple and quick detection of the explosive TATP would be very welcome.

BRIEF DESCRIPTION OF THE INVENTION

Figure 1:
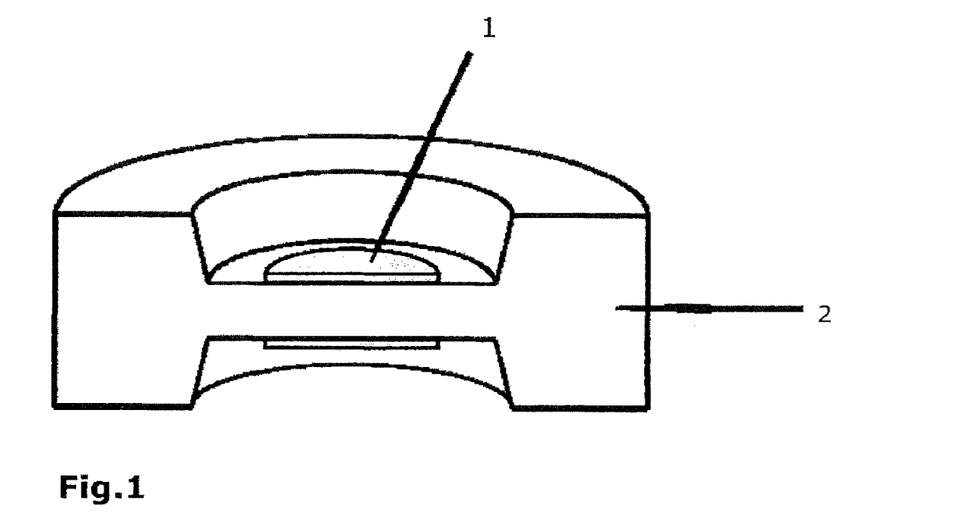
FIG. 1: Schematic structure of an HFF oscillating quartz crystal with an electrode (1) and quartz crystal (2).

It has now been found that a detection of TATP by means of a sensor technology can be effected on the basis of HFF oscillating quartz crystals. In principle, these are high fundamental frequency oscillating quartz crystals whose material thickness has been reduced in the center by means of "inverted mesa technology" (FIG. 1). The thinner region is contacted with metallic electrodes on both sides thereof, and using the inverted piezoelectric effect, it is excited with a high frequency that corresponds to the resonant frequency of the quartz crystal. The thus generated resonant vibration is directly dependent on the mass of the oscillator. Mass changes, for example, from adsorption, therefore lead to frequency changes that are easily measurable. Thus, the present invention relates to:

(1) a device for the online detection of triacetone triperoxide (TATP), comprising a measuring cell with at least three differently coated HFF oscillating quartz crystal sensors (sensors), one of the sensitive surfaces of each of the three oscillating quartz crystals being coated with a cyclodextrin derivative, a dimensionally stable dendrimer and a cholic acid derivative as detector substances; and (2) a process for the online detection of triacetone triperoxide (TATP), comprising contacting a device as defined above in (1) with the medium to be tested.

The device and the process of the invention enables a quick (i.e., direct, "online") and continuous detection of the explosive TATP from the ambient air. Thus, quick on-site examinations of people and objects for TATP traces become possible.

DETAILED DESCRIPTION OF THE INVENTION

Figure 2:
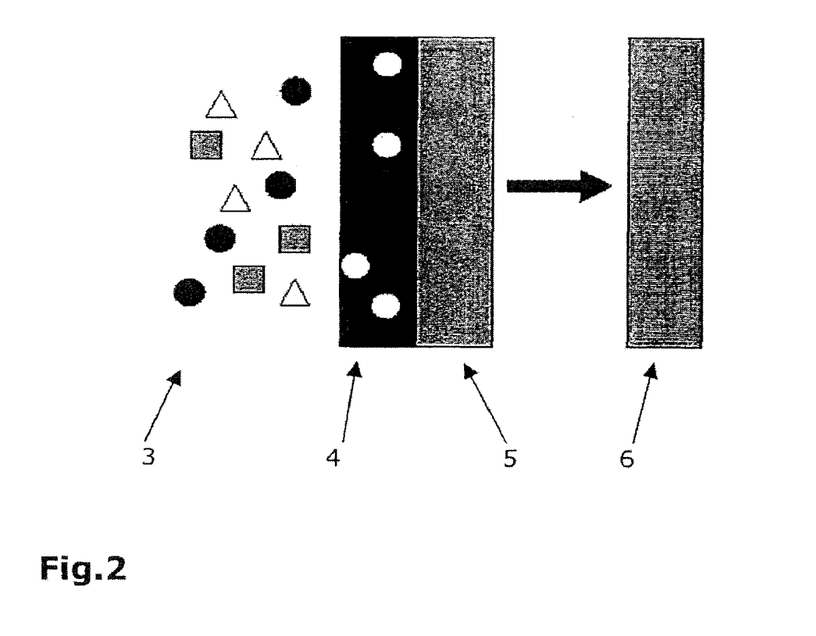
FIG. 2: Fundamental sensor construction according to the key-lock principle, wherein the analyte (3) binds to a selective receptor layer (4) and produces a signal in the electrode (6) through a transducer (5).

In the device according to aspect (1) of the invention, the sensors are coated with high-affinity acceptor substances in defined layer thicknesses to achieve chemical selectivity. Thus, a preselection of the analyte molecules is effected according to the key-lock principle (FIG. 2). Usually, such sensors do not respond exclusively to a single substance, but also to chemically similar substances. To eliminate such cross sensitivities and to reliably detect individual substances, several sensors are combined in a sensor array. Corresponding systems have already been described in the literature as "chemical noses".

Based on such experience, several sensors with different coatings are used, and their signals evaluated with chemometric methods. The less specific the sensor responses are, the more sensors become necessary. However, most arrays described in the literature must additionally make use of various enriching methods to achieve the necessary detection limit.

The invention makes use of a similar technology as that described, but due to the specific sensor combination, a time-consuming enrichment can be dispensed with. In combination with high-performance evaluation routines, a quick detection is possible in a single measuring step without additional enrichment.

The present invention is based on the development of a combination of coatings that yield a measuring signal from TATP traces in a highly selective and reversible way. This selectivity and sensitivity strongly simplifies the detection of TATP.

Only substances producing lipophilic cavity structures may be used as affinity materials (detector substances) (arrays are possible if orthogonal cross-sensitivities exist). The reliable identification of TATP is possible only with a combination of several sensors with different coatings into a sensor array. The minimum number of sensors required is three for the cross sensitivities examined hereby.

The combination of affinity materials employed in the sensors of the present invention consists of a cyclodextrin derivative, a dimensionally stable dendrimer and a cholic acid derivative. The amount of affinity material applied to the sensitive surface of the quartz crystal depends on the type of affinity material; preferably, the sensitive surfaces of the quartz crystals are coated with 10 to 350 ng, preferably 25 to 150 ng, of detector substance, which corresponds to a frequency lowering of 100 to 300 kHz.

Preferably, the cyclodextrin derivative is a β- or γ-cyclodextrin derivative, preferably perallyl-γ-cyclodextrin.

It is further preferred that the dimensionally stable dendrimer is a phenylene dendrimer, preferably a pyridine-containing terphenylene dendrimer of the 4th generation (Shifrina et al., Macromolecules 38(24): 9920-9932 (2005)).

Finally, it is preferred that the cholic acid derivative is a cholic acid salt, preferably sodium cholate.

A combination of sodium cholate (preferably with a 70 ng coating of the quartz crystal), octakis(2,3,6-tri-O-allyl)-γ-cyclodextrin (preferably with an about 35 ng coating of the quartz crystal) and the pyridine-containing terphenylene dendrimer MPI-7, i.e., the dendrimer of the 4th generation as described in Shifrina et al., Macromolecules 38(24): 9920-9932 (2005), of the formula shown below (Td-Gr-Ph)

-continued

-continued

-continued

Td-G4-Ph (preferably with an about 105 ng coating of the quartz crystal) has proven to be the most powerful combination and will be referred to as an optimum sensor array in the following and in the Experimental Examples. One of the great advantages of the system developed here is the fact that it can be dynamically extended to up to six sensors. Thus, it is possible to adapt the system to unexpectedly occurring cross-sensitivities without affecting its existing operating capacity.

Other oscillating quartz crystal sensors may be coated, for example with non-cross-linked polyurethanes (e.g., those prepared from conventional diisocyanates, such as toluene-2, 4-diisocyanate, and polyethylene glycol or polypropylene glycol), triphenylene ketals (e.g., triketals of hexahydroxytriphenylene (Waldvogel et al., Angew. Chem. 112(14), 2580-83 (2000)) and/or porphyrins (e.g., metalloporphyrins, such as Zn porphyrins).

Figure 3:
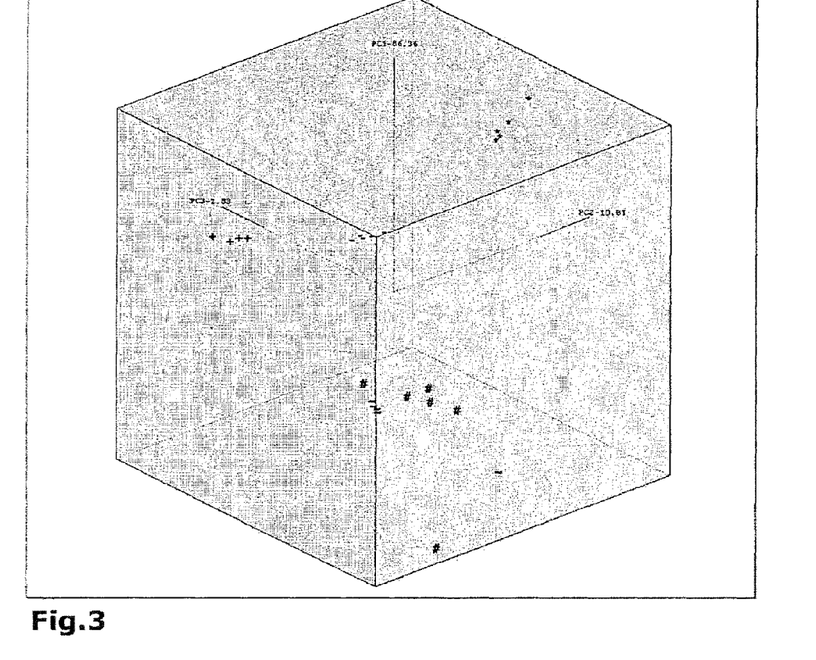
FIG. 3: Main component analysis of the five analytes using the sensor array (#=water; ~=hydrogen peroxide, -=bis(tert-butyl)peroxide; *=acetone; +=TATP).
Figure 4:
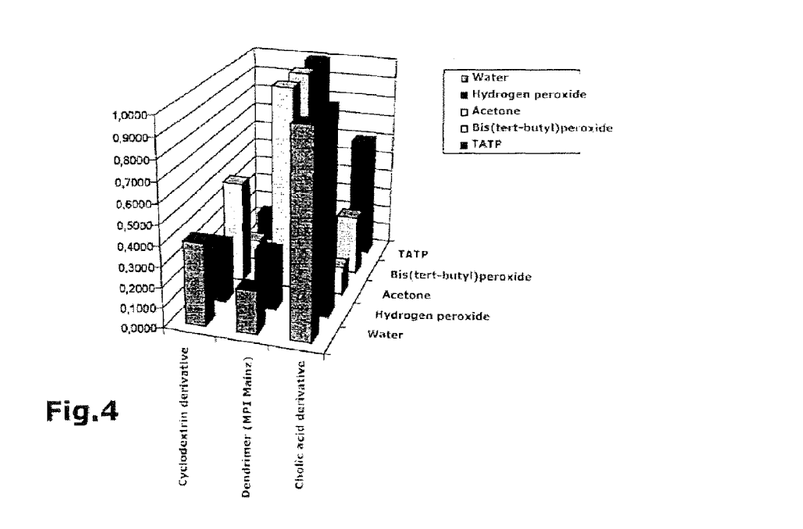
FIG. 4: Survey of the ratios of the sensor signals of TATP and different cross sensitivities (analyte concentration 1 ppm (v/v)).

The sensor array of the present invention is very selective and very sensitive. The combination with HFF oscillating quartz crystal technology and high performance evaluation algorithms (FIG. 3) allows for a quick online measurement. This allows very easily for a distinction between TATP and both chemically similar (bis(tert-butyl)peroxide) and structurally dissimilar cross sensitivities (FIG. 4). Thus, the invention is quick, continuous and selective.

Specific embodiments are characterized, for example, in that the signals from the individual sensors are recurred to for reducing the cross sensitivity (e.g., acetone or other peroxides). The evaluation algorithm subsequently provides for a selective measuring signal for the quantification of TATP.

In addition, the arrays (measuring units) are very small, so that they can be integrated into existing systems. Mass production is also conceivable since the material cost including electronics will probably be below €500.

Figure 5:
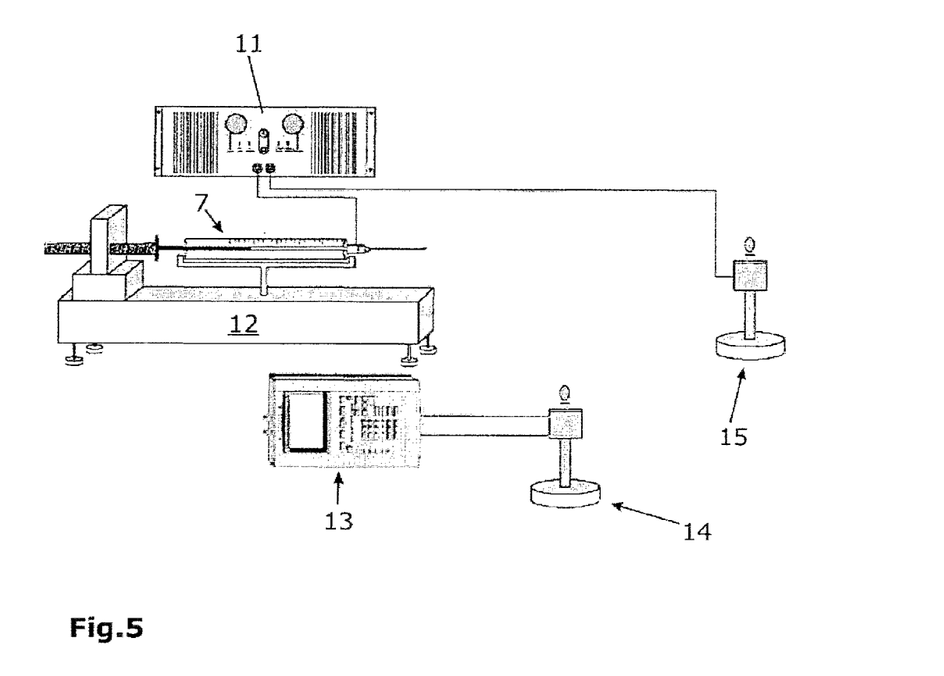
FIG. 5: Schematic construction of the coating unit (P. Mashayekhi, doctoral thesis, Bonn (2005)).
Figure 6:
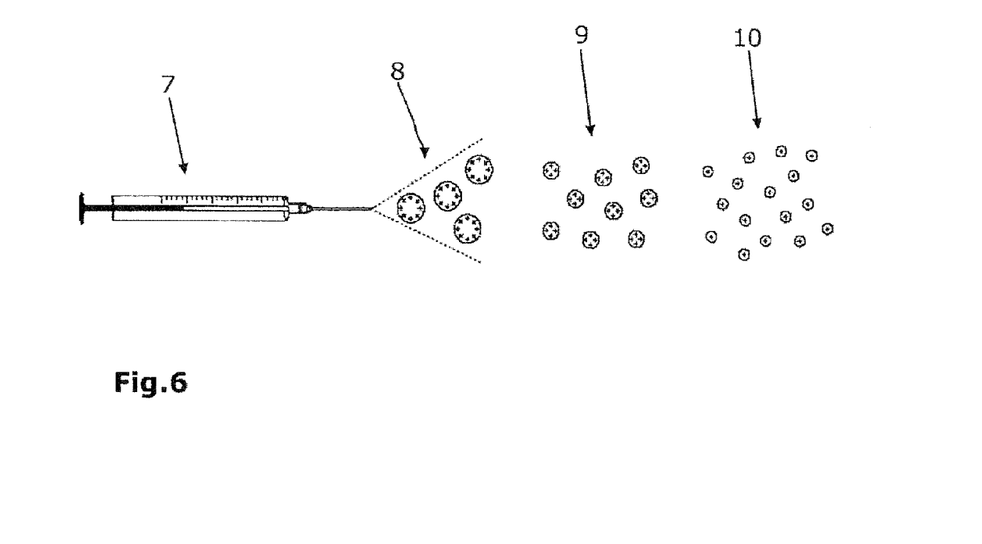
FIG. 6: Schematic representation of a Coulomb explosion according to Doyle with a Hamilton syringe 7, cone jet 8, satellite droplets 9 and microdroplets 10.

The coating of the sensitive surfaces of the quartz crystals was effected with a modified electrospray method (DE-A-103 44 135). FIG. 5 shows the schematic construction of a coating unit for oscillating quartz crystals (QCM) suitable for such a process. The course of the process is as follows: The substance to be coated is first dissolved in a volatile polar solvent, mostly methanol, the solution is taken up in a Hamilton syringe (7), which is then fixed on a step motor (12). Typically, a concentration of 30 µg/l is used in a 100 µl syringe. The positive pole is applied to the syringe cannula, and the negative pole is applied to the electrode of the target quartz (15). Between those, a high voltage of about 5 to 6 kV is applied by a potentiometer (11). The step motor slowly presses the solution out of the syringe. The solution is positively charged by the applied voltage and accelerated towards the electrode of the quartz crystal (14). According to the Coulomb explosion according to Doyle (DE-A-103 44 135; J. B. Fenn, Angew. Chem. 115, 3999-4024 (2003), see FIG. 6), the droplets are reduced in size on the way between the syringe and the electrode by the loss of solvent molecules, which continuously increases the charge density in the droplet and forms satellite droplets. This has the consequence that, from a critical radius, the Coulomb repulsion overweighs the surface tension, and the droplets virtually explode. Microdroplets are thus formed. In this way, only the pure substance arrives at the electrode. In this kind of coating, the layers are self-healing, since the receptor molecules impinging first form an insulating layer on the negatively charged electrode.

For the HFF quartz crystals employed, another slightly modified process is used. The spray cone is produced as described above, the quartz crystal to be actually coated being placed 10 to 15 cm beside the center of the spray cone. This is always necessary when the great mass sensitivity of the HFF quartz crystals would result in an immediate breakdown of the oscillation if they were coated directly. By appropriately selecting one of the two methods, it is possible to produce coatings of from 0 to 1000 kHz on the quartz crystals. With this method, coatings of from 0 to about 350 ng can be produced on the quartz crystals. The coating thickness can be monitored continuously with a frequency counter (13). This enables highly reproducible and comparable coatings.

In a preferred embodiment of the coating method, the electrospray coating is effected under reduced pressure (at about 200 mbar), which reduces the droplet formation.

Reproducible conditions are essential for comparing different affinities and for the calibration between the analyte and host substance. Therefore, a gas mixing system (see FIG. 7) that ensures such reproducibility was constructed from two modules (I, II). The first part of the system (I) is used to produce strictly defined analyte gas streams (20), and part II is a temperature-controlled measuring cell (28) for six quartz microbalances, connected to the analyte gas stream (20). Module I is assembled from four mass flow controllers 5850S (21=200 ml/min, 22=20 ml/min) of the company Brooks Instrument B. V. and a replaceable gas-washing bottle temperature-controlled to 20° C. With the mass flow controllers (21, 22), two controllable nitrogen gas streams (see 18 and 17) with a volume of from 1 to 200 ml/min can be withdrawn from a nitrogen cylinder (16). While stream (17) remains unchanged in temperature and composition, stream (18) is temperature-controlled to 20° C. (26) and passed through the gas-washing bottle (25). An analyte gas stream (17) having a broad range of analyte concentrations can be produced by recombining the two gas streams. The exact composition of the gas stream can be controlled by a personal computer using a serial interface.

Figure 7:
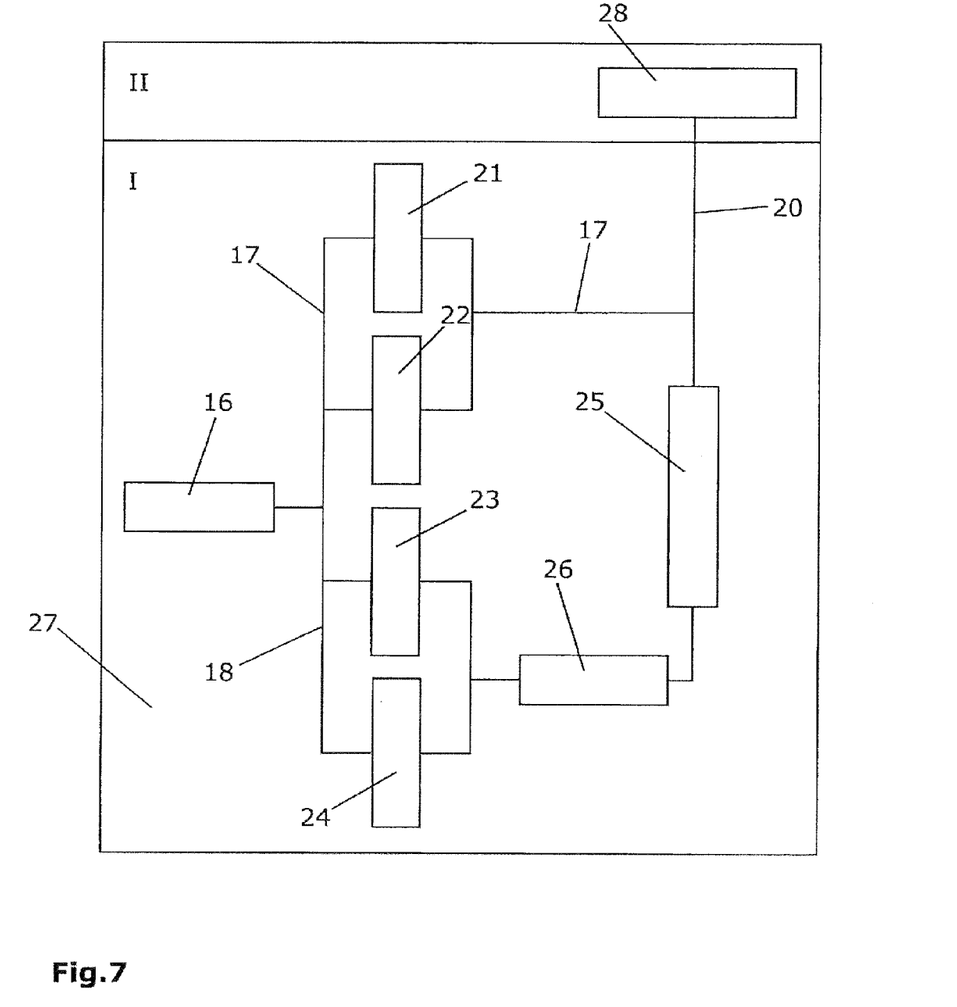
FIG. 7: Schematic construction of the gas mixing system.

For measuring samples that have a high vapor pressure (about 100 ppm) or can be employed in large amounts, the following method is employed. The production of sample gas (20) is effected by passing the nitrogen stream (18) through the analyte-filled gas-washing bottle, mixing it downstream thereof with the pure nitrogen stream (17). The gas-washing bottle (25) is temperature-controlled to 20° C., since the exact vapor pressure in known only at this temperature for most substances, which enables the concentration to be calculated. Since the two nitrogen streams (17, 18) can be controlled by means of the mass flow controllers (21, 22), concentrations having a volume proportion of from 0.5% to 100% of the maximum analyte saturation of the gas stream can be produced. From the mixing ratio, the volume-based concentration in ppm can be calculated very easily.

The actual sensor unit (FIG. 8, III) is constituted of a steel tube (V) and six sensor modules (IV). The sensor modules each contain an oscillator circuit by means of which the quartz crystal (29) mountable thereon is excited to vibrate. Further, they consist of frequency counters that are digitally readable through the USB interface. These sensor modules are introduced in the metal body and tightly screwed. The thus formed measuring cell has Swagelok ports (30) at the output, through which it can be connected with module I. Since the quartz microbalances (29) exhibit a temperature dependency, the measuring cell is constantly kept at 35° C. By selecting this temperature, it is ensured that it is always above room temperature. This measure prevents condensation effects, and at the same time the dynamics of the sorption processes remains comparable.

Figure 8:
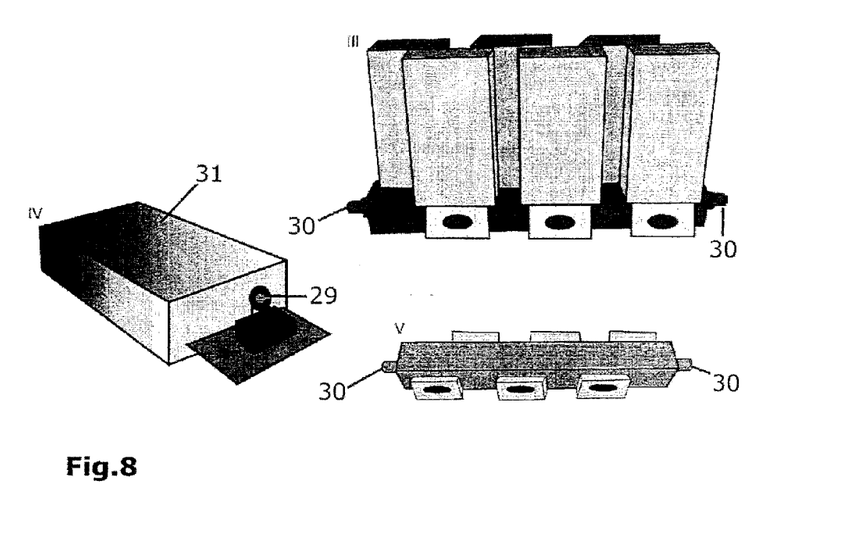
FIG. 8: Schematic construction of the measuring cell.

The electronics employed consists of a fixture for the quartz crystal (29), an oscillator (31) that excites the quartz crystal to vibrate, and a measuring unit (31) that can determine the exact vibration frequency of the quartz crystal by means of a processor (G. Sauerbrey, Verwendung von Schwingquarzen zur Wägung dünner Schichten and zur Mikrowägung, Z. Phys. 155, 206-222 (1959); Neubig, W. Briese, Das Grosse Quarzkochbuch, Franzis-Verlag Feldkirchen (1997)). The components can be connected in series through RJ 45 ports and read out by a personal computer using a USB adapter.

In a particular embodiment of the invention, two frequency counters per quartz crystal are provided. It has been found that a gate time of one second is necessary for an exact determination of integer frequencies for the frequency counters available today. Therefore, in order to achieve a higher sampling rate, the frequency counters provided per quartz crystal are started at intervals of 0.5 seconds and read out asynchronously. Of course, it is also possible to provide more than two frequency counters per quartz crystal, which are started at different time intervals in order to reach an even higher sampling rate.

The use of an FPGA (field-programmable gate array) in 90 nanometer technology as the electronics has proven particularly advantageous for processing the counting results. The counting algorithm and the further processing of the counting results are implemented by a combination of a VHDL design (Very High Speed Integrated Circuit Hardware Description Language) and an IP soft core within the FPGA. For example, such a circuit enables the parallel asynchronous 28-bit counting by three sensors with an accuracy of ±1 bit. This allows for a resolution of down to one Hertz.

The device for the online detection of triacetone triperoxide (TATP) may have a housing with an interior air channel, for example, the air channel being in communication with an aperture in the housing. Through this aperture, the air charged with analyte can be allowed to enter. The oscillating quartz crystals connected with the electronics can be provided in the air channel.

In order to enable an improved suction of the air, a suction device producing a reduced pressure in the housing may be provided. The suction device may be realized, for example, by a fan provided on the backside of the housing or by an external pump connected with the housing.

Since it is necessary that in-flowing air is supplied to the oscillating quartz crystals exclusively through the air channel, the housing should have a substantially air-tight design.

The device according to the invention may also be designed as a mobile appliance having a mobile power supply and a wireless data transmission for transmitting data to a computer, for example, a WLAN adapter.

Since temperature variations may lead to disturbances in the signal course, it may be provided that a fixture that enables a temperature equilibration of the in-flowing air is arranged on the aperture of the air channel. This fixture can be heatable, for example, so that the air flowing into the air channel is brought to a constant temperature by supplying external energy. Alternatively, it may be provided that a heat-conductive material having a large surface area is inserted in the fixture, so that the air flowing in through the fixture comes into contact with the material over a large surface area, whereby small temperature variations can be successfully reduced by an intensive heat exchange between individual regions of the in-flowing air. For example, it may be provided that several perforated plates of metal, for example, aluminum, through which the in-flowing air is passed are arranged in said fixture.

The invention is further illustrated by means of the following Examples. However, these do not limit the invention.

Examples

Materials and Methods

Quartz crystals employed: AT-cut HFF quartz crystals with a fundamental frequency of 195 MHz on an HC-52/U mount (product designation: Quarz * XA 1600 (ed. 06/05) RoHS-compliant product, HC-52/U, QF: 195 MHz; manufacturer: KVG Quartz Crystal Technology GmbH, Neckarbischofsheim, Germany).

Coating method: The coating was effected by a modified electrospray method (DE-A-103 44 135) with the coating unit for oscillating quartz crystals (QCM) as shown in FIG. 5. The substance to be applied was first dissolved in a volatile polar solvent (methanol), the solution was taken up in a Hamilton syringe at a concentration of 30 µg/l in a 100 µl syringe. The positive pole was applied to the syringe cannula, and the negative pole was applied to the electrode of the target quartz crystal. Between these, a high voltage of about 5-6 kV was applied by a potentiometer, the step motor pressing the solution slowly out of the syringe. The solution was positively charged by the applied voltage and accelerated towards the electrode of the quartz crystal.

The quartz to be coated was placed 10 to 15 cm beside the center of the spray cone. This is necessary since the high mass sensitivity of the HFF quartz crystals would lead to an immediate breakdown of the vibration if they were coated directly. The coating thickness was continuously monitored with a frequency counter.

Figure 12:
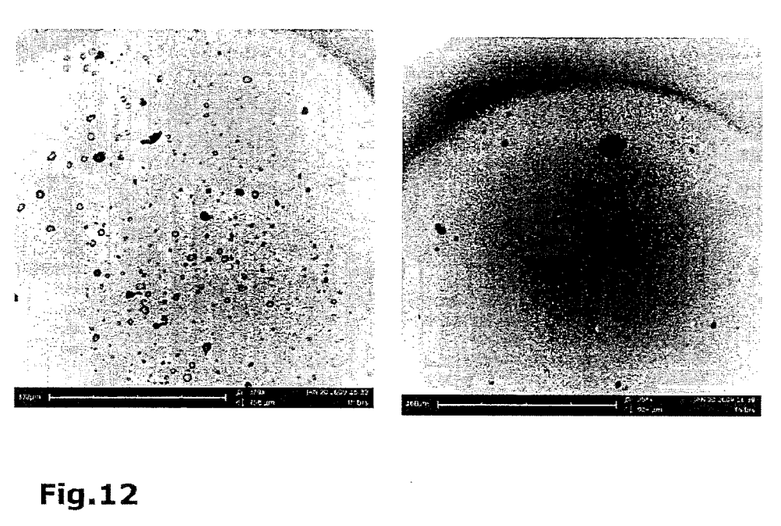
FIG. 12: Electron microscopic examination of coated quartz crystals. Coating at normal pressure (left) and under a reduced ambient pressure (right).

The above described coating method involves the problem that a significant droplet formation may occur, which ultimately results in an inhomogeneous appearance of the coating. Since this cannot be beneficial to the quality and reproducibility of the quartz crystal, the coating was performed under a reduced pressure. Thus, the syringe cannula is inserted in the inlet of a glass vessel that can be evacuated, which is brought to a pressure of 200 mbar by a continuously working pump. This glass vessel contains the quartz crystal to be coated and the counter electrode. The further construction remains the same as in the conventional coating method as described above. In FIG. 12, a quartz crystal coated by this modified method is compared to one prepared by the conventional method. Coatings prepared by the modified method are characterized by a significantly lesser number of large droplet traces on the surface.

Construction of the measuring device: For comparing different affinities and for the calibration between the analyte and host substance, reproducible conditions are essential. Therefore, the device consisting of two modules (I, II) as shown in FIG. 7 and the sensor unit as shown in FIG. 7, III, was used.

Measuring method: The testing gas was adjusted by dilution to concentrations of from 0.5 to 100% of the maximum possible content of the analyte-saturated gas stream. Thus, it was possible to determine the isotherm at 35° C. whose slope in Hz/vol·ppm could be compared to the isotherms of other analytes.

All the ppm values stated below are based on these volume ratios.

Production of TATP samples: "Real explosives micro portion specimens (EMPK)" from the company "Dülsner Sicherheitstechnik (Köln)" in two variants, 0.5 mg and 2.0 mg of TATP, were used as the TATP source. Due to this low amount of substance in combination with the slow desorption rate from the EMPK, it was necessary to produce gas samples of a defined concentration. Thus, in the case of the EMPK coated with 0.5 mg of TATP, two specimens were placed in a closed glass vessel (solvent ball from column chromatography) having a volume of 2.3 l for at least 6 hours. In this time, the TATP present on the specimens will desorb completely, and a gas sample having a defined concentration of 44 ppm is formed. This method could be used as long as the desired concentration is below the TATP vapor pressure of 68.5 ppm at 25° C. In the EMPK coated with 2.0 mg of TATP, only one specimen is placed in a vessel having a volume of 4.5 l. The desorption also forms a gas mixture with a concentration of 44 ppm TATP. In the experimental set-up, these sample gas containers can be replaced by the gas washing bottle and diluted by admixing gas stream (m).

Data evaluation: The evaluation of the data is effected in real time using Matlab (R2007b) from the company "Math Works". Thus, the recorded data are directly normalized in order that the ratios between the signals rather than their absolute values can be considered. Subsequently, the thus processed data are subjected to a main component analysis (function implemented in the program) by which the signals are assigned to a region in a two-dimensional coordinate system. For the substance identification of the analyte, the thus established region is compared to that of defined analyte samples.

High-affinity materials: A combination of sensors is employed which are coated with sodium cholate (70 ng; commercially available from FLUKA), octakis(2,3,6-tri-O-allyl)-γ-cyclodextrin (35 ng; A. Leydet et al., J. Med. Chem. 41, 4927-4932 (1998) and J. Ni et al., Carbohydr. Res. 337, 217-220 (2002)) or phenylene dendrimer MPI-7 (105 ng; e.g., Shifrina et al., Macromolecules 38, 9920-9932 (2005)).

Figure 9:
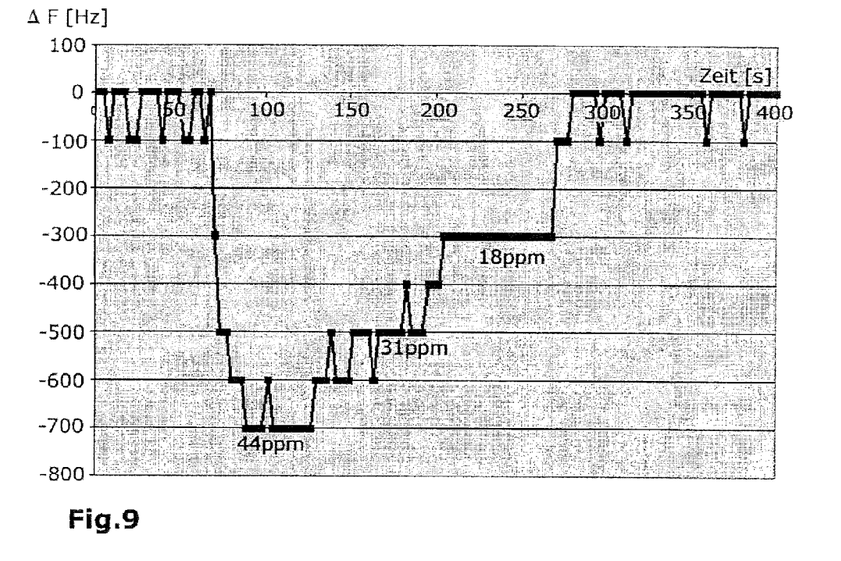
FIG. 9: Serial concentrations of a quartz crystal coated with 10 ng of octakis(2,3,6-tri-O-methyl)-γ-cyclodextrin with TATP.

Measuring results: For the measurement, the signals of the individual sensor elements were continuously recorded, and the frequency change as compared to the baseline was observed. To establish the reference data sets for analyte identification, serial concentrations for the analytes were measured with the receptor substances in the measuring device described, and the signal was respectively determined in the equilibrium. Serial concentrations of a quartz sensor coated with 10 ng of octakis(2,3,6-tri-O-allyl)-γ-cyclodextrin with TATP are shown in FIG. 9.

Example 1

Affinity Examination of Analytes

The affinity of different coatings for TATP was examined. Thus, in addition to triacetone triperoxide (TATP), water, hydrogen peroxide solution (30%) and acetone were considered as potential cross sensitivities, and in addition, bis(tert-butyl)peroxide was considered due to its structural similarity with TATP. For these five analytes, serial concentrations were measured at a sensor temperature of 35° C., and the isotherm was respectively determined.

The concentration range in which the analytes were measured is mainly defined by their vapor pressures at 20° C. A survey of the analytes employed, their vapor pressure and the measured concentration ranges is shown in Table 1.

TABLE 1

Survey of the examined analytes

| Analyte | Vapor pressure [ppm (v/v)] | Concentration range [ppm (v/v)] |
|---|---|---|
| Water | 23,000 (at 20° C.)* | 1150-6900 |
| $H_2O_2$ (30%) | 14,500 (at 20° C.)** | 725-4350 |
| Acetone | 245,310 (at 20° C.)*** | 12,265-73,593 |
| Bis(tert-butyl)peroxide | 53,329 (at 20° C.)*** | 2666-15,999 |
| Triacetone triperoxide | 68.5 (at 25° C.)**** | 3-44 |

*Information provided by the manufacturer, Chemikalien Reagenzien, Merck (2003);
**W. Schumb et al., Hydrogen Peroxide, Reinhold Publishing Corporation, New York (1955);
***Information provided by the manufacturer, Hand-buch Feinchemikalien, Aldrich (2007);
****J. C. Oxley et al., Propellants, Explosives, Pyrotechnics 30, 2, 127-130 (2005).

Example 2

Detection in an Open System

Figure 10:
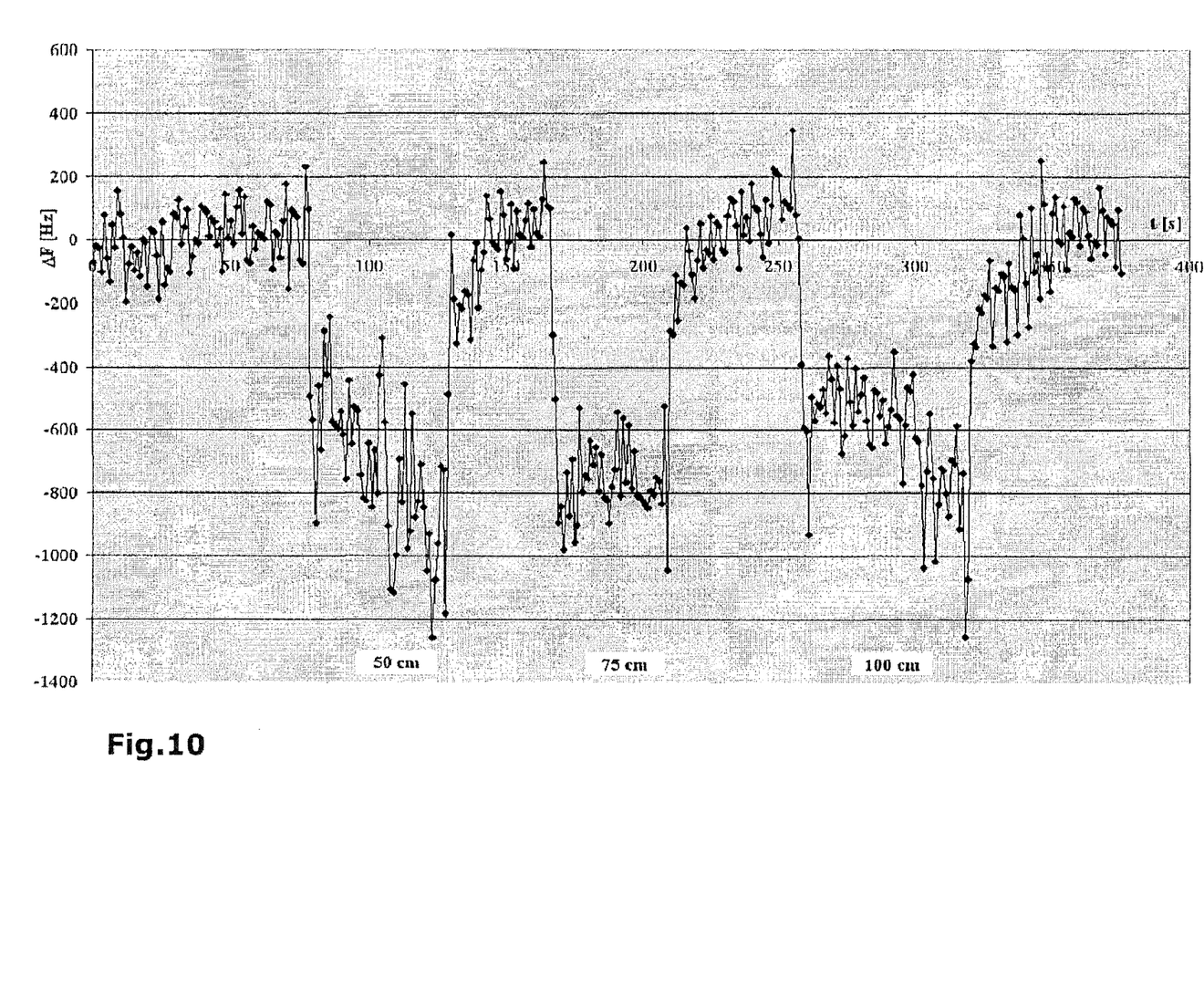
FIG. 10: Blow-on examinations at different distances (coating, polyurethane 105 ng) with a model analyte.

An open system was designed for measurements in an open system with a distance between the analyte source and the sensor array. Thus, a fan is installed in a duct or an air lock opposite the sensor, and an air stream directed against the sensor is generated (about 2 m/s). This air stream conveys analytes to the sensor very quickly and with a relatively low dilution rate over a distance of about 1 m. In the following, the model analyte phenol is shown, which has a vapor pressure comparable to that of TATP. Almost independently of the distance, the examinations show a signal build-up within 2-4 seconds (FIG. 10).

Example 3

Temporal Resolution/Identification of TATP

Figure 11:
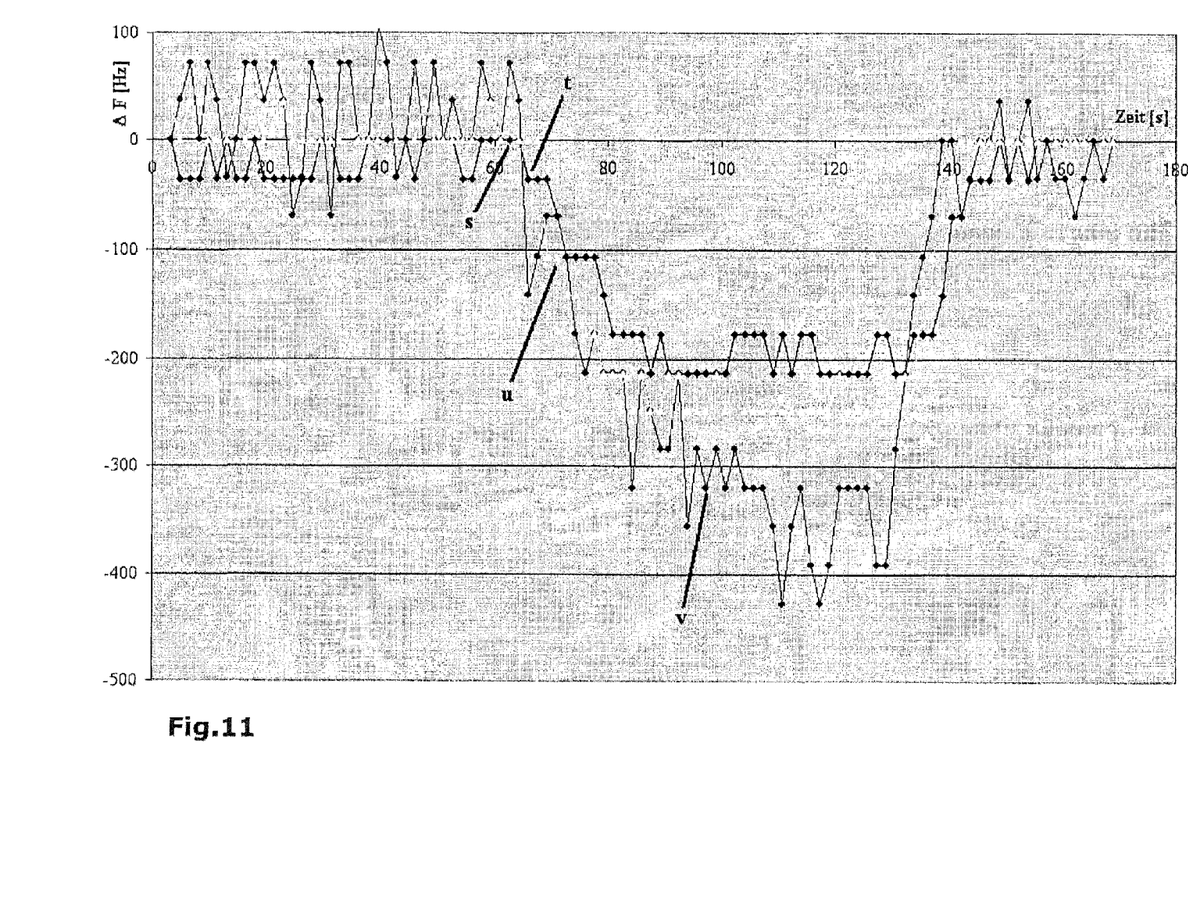
FIG. 11: Temporal recognition of a TATP signal at a concentration of 35 ppm with the optimum sensor array.

The sensor array described in this patent exhibits very fast response times for the reliable identification of a signal. Three seconds after the addition (s), a first response (t) by the sensors can already be seen. This three seconds is the apparatus-related dead time of the system. At the time (u) (5 s later), the signals are already sufficiently distinctive for a reliable identification. This time is way before the equilibrium of the incorporation (v). The results are summarized in FIG. 11.

The invention claimed is:

1. A device for the online detection of triacetone triperoxide (TATP), comprising a measuring cell with at least three differently coated high fundamental frequency oscillating quartz crystal sensors, the three oscillating quartz crystals each having a sensitive surface coated with a coating of a detector substance selected from a cyclodextrin derivative, a dimensionally stable dendrimer and a cholic acid derivative, the coating on the sensitive surface of each one of the three oscillating quartz crystals being different from the coatings on the sensitive surfaces of the other two of the three oscillating quartz crystals.

2. The device according to claim 1, wherein
(i) said cyclodextrin derivative is β- or γ-cyclodextrin derivative; and/or
(ii) said dimensionally stable dendrimer is a phenylene dendrimer; and/or
(iii) said cholic acid derivative is a cholic acid salt.

3. The device according to claim 1, wherein said measuring cell contains one or more further high fundamental frequency oscillating quartz crystal sensors coated with noncross-linked polyurethanes, triphenylene ketals and/or porphyrins on the sensitive surfaces.

4. The device according to claim 1, having a high fundamental frequency oscillating quartz crystal sensor coated with sodium cholate, with a coating rate of about 70 ng, a high fundamental frequency oscillating quartz crystal sensor coated with octakis(2,3,6-tri-O-allyl)-γ-cyclodextrin, with a coating rate of about 35 ng, and a high fundamental frequency oscillating quartz crystal sensor coated with phenylene dendrimer, with a coating rate of about 105 ng.

5. The device according to claim 1, wherein the sensitive surfaces of the quartz crystals are coated with 10 to 350 ng of detector substance, which corresponds to a frequency reduction of the quartz crystals of from 100 to 300 kHz.

6. The device according to claim 5, wherein said coating is effected by an electrospray method in which the detector substance is dissolved in a volatile polar solvent and accelerated towards the sensitive surfaces of the quartz crystal by applying a high voltage.

7. The device according to claim 6, wherein said electrospray method is effected below atmospheric pressure.

8. The device according to claim 1, further containing at least one frequency counter and at least one evaluator unit.

9. The device according to claim 8, wherein at least two frequency counters per quartz crystal are provided, which can be operated asynchronously.

10. A process for the online detection of triacetone triperoxide (TATP), comprising contacting a device according to claim 1 with a medium to be tested, detecting a response produced in the three oscillating quartz crystals of the device when the medium is contacted with the device and correlating said response to the presence of TATP in the medium.

11. The process according to claim 10, wherein the medium is ambient air, and the process has a TATP sensitivity of <10 ppm in the ambient air and requires no enrichment of the TATP.

12. The process according to claim 10, which further comprises a comparison of a response produced in the three oscillating quartz crystals of the device when the medium is contacted with the device and a response produced in the three oscillating quartz crystals of the device when a reference substance or a mixture of reference substances is contacted with the device.

* * * * *